(12) United States Patent
Schecter

(10) Patent No.: US 7,805,194 B1
(45) Date of Patent: Sep. 28, 2010

(54) MATRIX OPTIMIZATION METHOD OF INDIVIDUALLY ADAPTING THERAPY IN AN IMPLANTABLE CARDIAC THERAPY DEVICE

(75) Inventor: Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 809 days.

(21) Appl. No.: 11/556,552

(22) Filed: Nov. 3, 2006

(51) Int. Cl.
*A61N 1/00* (2006.01)

(52) U.S. Cl. ....................................................... 607/17

(58) Field of Classification Search ............. 607/17–19, 607/2, 6, 9, 14, 20, 23–25; 600/510, 437; 604/27; 702/19
See application file for complete search history.

(56) References Cited

U.S. PATENT DOCUMENTS

| | | | | |
|---|---|---|---|---|
| 5,129,394 A | * | 7/1992 | Mehra | 607/23 |
| 5,269,301 A | * | 12/1993 | Cohen | 607/6 |
| 5,730,720 A | * | 3/1998 | Sites et al. | 604/27 |
| 5,904,708 A | * | 5/1999 | Goedeke | 607/18 |
| 6,223,082 B1 | | 4/2001 | Bakels et al. | |
| 6,238,420 B1 | | 5/2001 | Bakels et al. | |
| 6,871,088 B2 | | 3/2005 | Chinchoy | |
| 7,610,088 B2 | * | 10/2009 | Chinchoy | 607/17 |
| 2001/0010009 A1 | | 7/2001 | Bakels et al. | |
| 2002/0143368 A1 | | 10/2002 | Bakels et al. | |
| 2003/0199930 A1 | | 10/2003 | Grandjean | |
| 2003/0199934 A1 | | 10/2003 | Struble et al. | |
| 2003/0204212 A1 | | 10/2003 | Burnes et al. | |
| 2004/0186524 A1 | | 9/2004 | Chinchoy | |
| 2005/0038481 A1 | | 2/2005 | Chinchoy et al. | |
| 2005/0043895 A1 | * | 2/2005 | Schechter | 702/19 |
| 2005/0131469 A1 | | 6/2005 | Cohen | |
| 2005/0137630 A1 | | 6/2005 | Ding et al. | |
| 2005/0182447 A1 | * | 8/2005 | Schecter | 607/2 |
| 2005/0209519 A1 | * | 9/2005 | Krishnan et al. | 600/437 |

FOREIGN PATENT DOCUMENTS

| | | | |
|---|---|---|---|
| WO | 2005018570 | A2 | 3/2005 |
| WO | 2005018570 | A3 | 3/2005 |
| WO | 2005018740 | A1 | 3/2005 |
| WO | 2005020025 | A2 | 3/2005 |
| WO | 2005020025 | A3 | 3/2005 |
| WO | 2005123178 | A2 | 12/2005 |
| WO | 2005123178 | A3 | 12/2005 |

\* cited by examiner

*Primary Examiner*—George Manuel
*Assistant Examiner*—Robert N Wieland

(57) ABSTRACT

A system and method of adjusting therapy delivery in an implantable cardiac stimulation device including establishing a plurality of setting combinations for at least two variable parameters of the implantable cardiac stimulation device affecting delivery of therapy. At least one aspect of a patient's physiologic performance is evaluated under individual ones of the plurality of setting combinations selected such that at least one of the two variable parameters vary among the plurality of combinations. A setting combination providing more optimal patient physiologic performance is programmed for future delivery of therapy. An external device can provide measurements indicative of cardiac performance. Measurements of cardiac performance can also be obtained by an implantable device.

9 Claims, 14 Drawing Sheets

MATRIX OPTIMIZATION METHOD OF INDIVIDUALLY ADAPTING THERAPY IN AN IMPLANTABLE CARDIAC THERAPY DEVICE

FIELD OF THE INVENTION

The invention relates to the field of implantable cardiac stimulation devices and more particularly to individually optimizing or adapting multiple independent variables determining therapy delivery provided by an implantable cardiac stimulation device to provide improved synchronization of various regions of contractile tissue.

BACKGROUND OF THE INVENTION

Numerous people suffer from physical ailments affecting their heart function. Patients having diseased myocardium often exhibit impairment of the normal physiologic conduction system, myocardial stunning, hibernation, and/or myocardial necrosis. Of these symptoms, myocardial stunning, hibernation, and necrosis generally lead to hypocontractility of the cardiac muscle. Many patients also exhibit reduced cardiac output as a secondary symptom of a lack of myocardial contractility, impaired conduction, and/or deficiencies in the synchronicity of cardiac depolarization/repolarization. These factors generally result in impaired systolic and/or diastolic function which results in the commonly named congestive heart failure (CHF) or simply heart failure (HF).

Accordingly, a variety of therapies, including therapies automatically provided by therapeutic devices, have been developed and continue to be further developed for treatment of patients, including patients suffering from HF. One particular category of therapy which has been developed is provided by implantable cardiac stimulation devices. Such cardiac stimulation devices are frequently configured to be implanted in order to provide long term automatic monitoring of the patient's condition and to generate and deliver therapeutic cardiac stimulation as indicated. Implantable cardiac stimulation devices have been developed to monitor and provide therapy independently to multiple locations of the patient's heart, including multiple chambers of the patient's heart.

One particular category of implantable cardiac stimulation devices includes the ability to monitor activity in and selectively deliver therapy to both of the patient's ventricles. This is frequently referred to as bi-ventricular or bi-V therapy. Implantable cardiac stimulation devices configured for bi-ventricular stimulation can be further configured to provide cardiac resynchronization therapy (CRT). CRT refers to modes of therapy which strive to restore a more closely normal synchronization between the patient's right and left ventricles. While CRT is as yet not effective with all patients suffering from HF, for many HF patients, CRT can improve the overall pumping effectiveness of an HF patient and thereby improve their quality of life. In at least certain patients, CRT can at least partially compensate for conduction/stimulation deficiencies to thereby improve synchronization of the electrical stimulation of the myocardium and to at least partially compensate for myocardial tissue having impaired contractility.

While CRT has been shown to provide valuable benefits to certain HF patients, there remains a sizeable portion of the HF population that has been non-responsive or at best less responsive to existing CRT systems and algorithms. Thus, it will be appreciated that there exists needs for improved systems and methods of delivering cardiac therapy both to improve the efficacy for patients who have exhibited positive response, as well as to provide new types of therapy for those patients who have exhibited less beneficial response. It would be beneficial to provide improved systems and methods of providing therapy that would be generally compatible with existing hardware platforms. It would be further advantageous to provide innovative systems and methods of providing therapy that would be compatible with improved hardware platforms.

SUMMARY

Aspects of the invention include implementation of individually adapted therapy. The implementation can be conceptualized in some embodiments as a matrix based approach to evaluating multiple independent parameters. Certain implementations can include use of a non-implantable diagnostic tool employed in concert with an implantable device and certain implementations can proceed post-implantation in a closed loop manner via action of the implantable device.

One embodiment includes a method of adjusting therapy delivery in an implantable cardiac stimulation device, the method comprising establishing a plurality of setting combinations for at least two variable parameters of the implantable cardiac stimulation device affecting delivery of therapy, evaluating at least one aspect of a patient's physiologic performance under individual ones of the plurality of setting combinations wherein the plurality of setting combinations are selected such that at least one of the two variable parameters vary among the plurality of combinations, and selecting a setting combination providing more optimal patient physiologic performance.

Another embodiment includes a therapeutic stimulation system comprising an implantable cardiac stimulation device comprising an implantable stimulation generator and at least one implantable lead adapted for connection to the implantable stimulation generator and further adapted for at least one of sensing physiologic activity and delivery of therapy and a controller in communication with the at least one implantable lead and stimulation generator and configured to automatically evaluate a patient's physiologic status and selectively induce delivery of therapeutic stimulation under at least two variable therapy parameters and wherein the system determines at least one measure of a patient's cardiac performance and evaluates the patient's cardiac performance under a plurality of different combinations of the at least two variable therapy parameters and configures the implantable device with a combination of the at least two variable therapy parameters exhibiting greater cardiac performance. These and other objects and advantages of the invention will become more apparent from the following description taken in conjunction with the accompanying drawings.

BRIEF DESCRIPTION OF THE DRAWINGS

FIG. 1 also illustrates waveforms corresponding to a patient's physiologic parameters including cardiac strain curves and a surface ECG curve.

DETAILED DESCRIPTION OF THE PREFERRED EMBODIMENTS

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
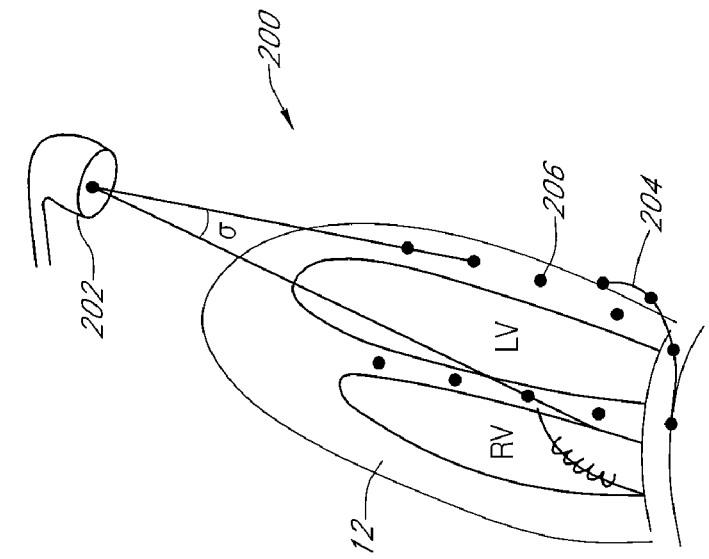
FIG. 1 illustrates one embodiment of a system for monitoring physiologic parameters of a patient, including in this embodiment both external and implanted measuring systems.
Figure 1:
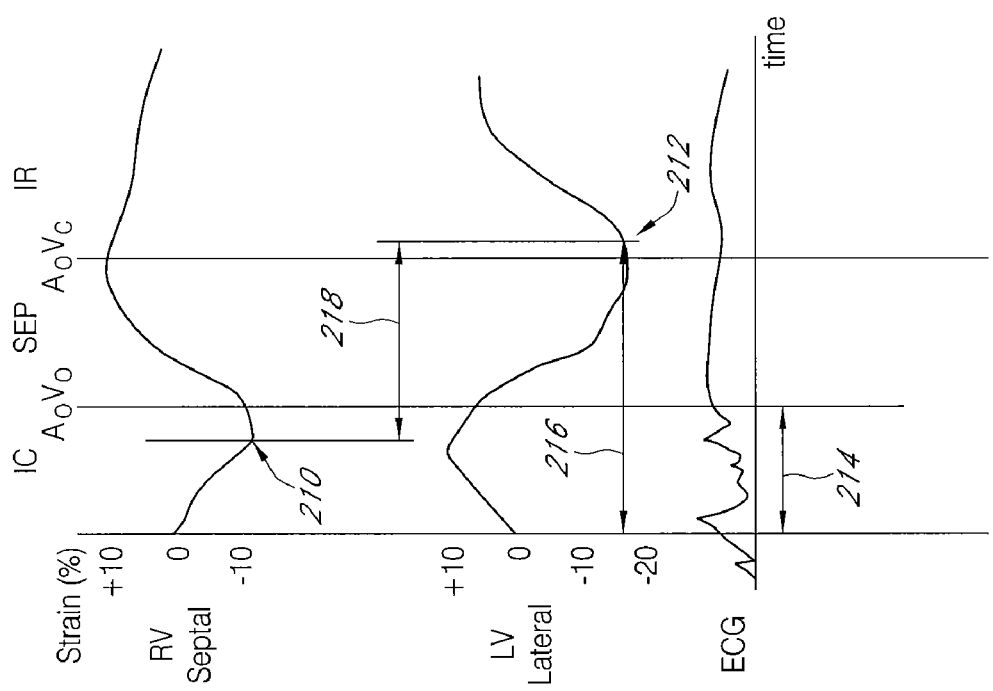

FIG. 1 illustrates schematically one embodiment of a therapy system 200 configured to measure and evaluate a patient's physiology and further adapted to adjust therapy delivery in an individualized manner to optimize the therapy for the needs and condition of the individual patient. As used herein, the terms "optimal", "optimize," "optimizing," "optimization", "minimize", "maximize" and the like are to be understood as commonly used terms of the art referring simply to a process of evaluating and adjusting or individualizing the operating parameters of a system for improved performance in an individual application. It will be understood that the physiologic activity and characteristics of an individual, for example their cardiac activity, is subject to both cyclical variations, diurnal variations, and long term variations. An individual patient's physiologic activity is also subject to variation brought about by medication dosing and environmental factors or noise which are generally asynchronous and unpredictable by an automated therapy system. Thus, the matching of therapy systems and methods to precise instantaneous needs of a patient is as a practical matter an inexact science. Thus, use of the terms "optimal", "optimize," "optimizing," "optimization" and the like does not imply that the described process results in a perfect setting for a system or method as used with an individual patient or that any further improvements are not available. Thus, the terms "optimize," "optimizing," and/or "optimization" are to be interpreted as relative terms indicating generally improved performance in an individual application and are not to be interpreted as absolutes.

In this embodiment, the system 200 includes one or more external measurement systems 202 and one or more measurement systems 204 adapted for internal measurements, e.g., from an implanted environment. In one embodiment, the external measurement system 202 includes an imaging system, such as an ultrasonic imager. In one particular embodiment, the external measurement system 202 generates and delivers ultrasonic vibrations which extend generally within a cone defined by an angle of ultrasonic insonification Θ. In this embodiment, the external measurement system 202 directs the ultrasonic vibrations from an apical aspect of the patient's heart 12 to develop apical four chamber echocardiograph view of the patient's heart physiology.

In this embodiment, the system also includes one or more physiologic sensors 204 configured for internal sensing of the patient's physiology. In one embodiment, the internal sensors 204 include a multi-site coronary sinus (CS) lead and a right ventricular (RV) mid-basal septal lead. The internal sensing system 204 is adapted to measure activity and/or characteristics at regions of interest 206. FIG. 1 illustrates that in one embodiment the regions of interest 206 include various regions of the patient's heart 12, for example including septal and lateral wall regions.

In certain implementations, preferred locations for ventricular electrodes are adjacent the RV septum (Basal or High Septum) and the lateral LV wall via a bipolar CS lead. These locations provide data which is more congruent with data acquired ultrasonically, such as via the imager system 202. In other implementations, a preferred placement for RV leads is in the RV septal location. In other implementations, an electrode is preferably engaged with the septum with the RV coil electrode arranged in the RV apex. In yet other embodiments, RV apical leads can be used but may be less preferred.

FIG. 1 illustrates the regions of interest 206 schematically via solid black dots arranged at various locations of the patient's heart 12. It will be understood that in particular implementations, the regions of interest 206 would not constitute true points but would rather encompass a spatially extending volume or region of the patient's tissue. It will be further understood that the particular arrangement of the internal sensing system 204 as well as the measurements taken with one or more external sensing systems 202 would be adapted to the particular needs/concerns for the individual patient.

FIG. 1 also illustrates exemplary waveforms indicative of one embodiment of measurements which can be made with one or more embodiments of the system 200. In this particular embodiment, FIG. 1 illustrates waveforms corresponding to strain measurements of an RV septal view over time as well as an LV lateral view over time. In other embodiments, one or more external sensing systems 202 can be utilized to develop measurements of the first derivative of strain, strain'. FIG. 1 also illustrates that in this embodiment an additional surface based measurement of a surface electrocardiogram (ECG) has also been developed and is illustrated coincident with the two strain waveforms corresponding to the RV septal and LV lateral views.

FIG. 1 also illustrates that various phases of the patient's cardiac cycles can be identified or delineated in the illustration of the time varying strain and ECG wave forms. More particularly, in one embodiment an isovolumic contraction (IC) region is defined as well as an isovolumic relaxation (IR) phase. Interposed between the IC and IR regions is a systolic ejection phase (SEP) with the boundaries of the respective regions delineated by respective valvular closing/opening events. The wave forms of FIG. 1 also illustrate certain identifiable characteristic monuments corresponding to physiologic activity. In this embodiment, a first monument 210 indicates maximal septal contraction before AV opening ($A_oV_o$). A second monument 212 corresponds to maximal lateral wall contraction after AV closure ($A_oV_c$).

In certain embodiments, the system 200 facilitates analysis of structural parameters of physiologic activity such as strain and/or strain rate, for example obtained by the external sensing system 202. In one embodiment, an external sensing system 202 including an ultrasonic sensor can obtain physiologic data from regions of interest 206 arranged in the interventricular septum and LV lateral wall to provide valuable information for optimizing synchronization and for reduction of pre and/or post-systolic myocardial thickening PSMT. Data derived from the system 200 can also be utilized in more effectively interfacing external sensing systems and other external devices. Additional details of preferred embodiments of such interfacing and various systems and methods of measuring a patient's physiologic performance can be found in the co-owned application (Ser. No. 11/748,894, titled "MEDICAL EVALUATION AND THERAPY SYSTEM FOR OPTIMIZING CARDIAC ELECTRO-MECHANICAL SYNCHRONY," and now abandoned), which is incorporated herein in its entirety by reference.

In certain embodiments for purposes of optimizing AV and RV-LV timing, structural physiologic data, such as acquired with ultrasonic measurements, is gathered while adjusting various interval timing parameters. Such measurement can be preferably performed over multiple cardiac cycles and the data gathered thereby further processed by summation averaging or ensemble averaging techniques to provide more representative data better accommodating for noise interference. One or more structural physiologic parameters, for example including myocardial velocity, strain, and/or strain rate can be estimated, for example from spatial gradients of velocity profiles acquired by color myocardial Doppler imaging (CDMI) for one or more regions of interest 206. As an example, integration of regional strain rate curves enables assessment of myocardial shortening and lengthening as well as estimation of myocardial strain.

FIG. 1 illustrates that in one embodiment several electromechanical parameters can be defined to characterize a patient's physiologic activity. In one embodiment, a time interval can be defined from the onset of systole, for example as defined by a surface ECG or IEGM, to peak RV strain as measured in a region of interest 206 preferably located in the basal portion of the interventricular septum or alternatively in a mid-region of the interventricular septum. This time interval can be abbreviated as t Strain RV identified on FIG. 1 by the reference designator 214. In certain implementations it will be preferred to examine the electrically based signals indicating onset of systole, for example ECGM and/or IEGM signals to account for peaks related to isovolumic contraction.

A similar electromechanical time interval t Strain LV 216 can be defined as the time interval from systole onset to peak LV strain which in one embodiment is preferably measured by a bipolar CS lead arranged adjacent the lateral wall of the LV. Use of a multi-site lead 204 can provide information from different locations for more precise location of an electrode proximal a region of interest 206 as well as providing greater flexibility in accommodating optimal locations for pacing stimulation. In this embodiment, a third mechanical timing interval between the RV and LV indicative of V to V timing is indicated as $\Delta V_r V_l$ 218.

In one embodiment, these timing intervals are used to derive and define one or more dimensionless correction factor indices. In one embodiment, a strain correction factor index (SCFI) 220 (FIG. 2) is defined as the ratio of $$\frac{T\ strain\ RV\ 214}{T\ strain\ LV\ 216}.$$

Optimal resynchronization will occur as SCFI 220 approaches a value of 1 or as $\Delta V_r V_l$ 218 approaches 0. It will expected that even during optimal conditions SCFI 220 will not necessarily equal 1 as not only will there be expected variable amounts of delayed temporal and spatial regional conductivity, but also myocardial segments with variably delayed anisotropic contractility. In order to achieve a correction factor index, such as a strain correction factor index SCFI 220 closer to 1, pre-activation of either of RV lead stimulation electrodes or LV lead stimulation electrodes is implemented depending upon the particular conditions of the individual patient. A larger $\Delta V_r V_l$ 218 or an SCFI 220 further from 1 will indicate a larger amount of pre-activation of RV or LV stimulation. Again, while it is expected that even with most optimal settings, for certain patients an SCFI 220 value will not necessarily equal 1, an advantageous end result can be achieved with synchronicity of RV and LV peak contractility between the basal septum and lateral wall indicated by an SCFI approaching 1.

Figure 2:
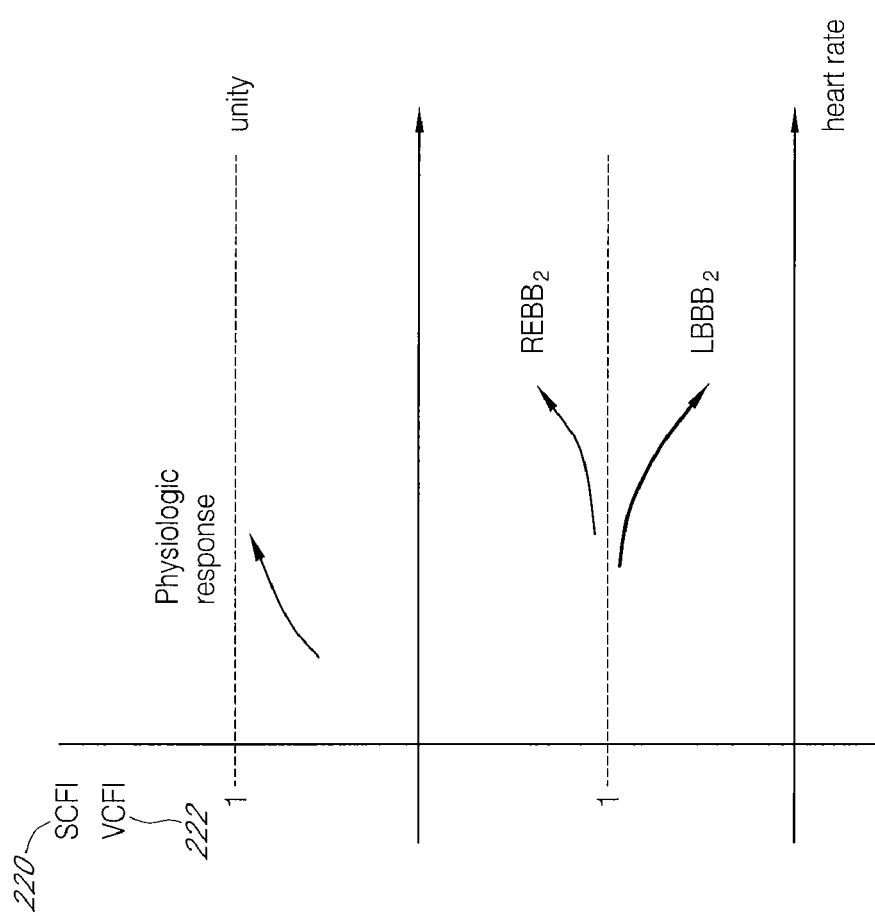
FIG. 2 illustrates schematically variation in several embodiments of a correction factor index as a function of changing heart rate, for example during exercise or Dobutamine medication.

FIG. 2 illustrates additional aspects of the system 200 illustrating rate dependency of correction factor indices. More particularly, FIG. 2 illustrates schematically variations of a correction factor index for various heart rates. For example, the patient's heart rate would be expected to vary with differing metabolic needs for rest periods as opposed to periods of exercise. Similarly, the patient's heart rate would be expected to vary under Dobutamine medication. FIG. 2 illustrates these variations for the previously described SCFI 220 as well as for a comparable velocity correction factor index 222. The VCFI 222 is a similarly dimensionless index corresponding to the ratio of right ventricular velocity to left ventricular velocity.

For example, it would be expected that SCFI 220 or VCFI 222 will not exhibit a constant value for varying heart rates, but rather will change in a generally asymptotic fashion as a function of heart rate as RV to LV intervals will narrow with elevated heart rates. Likewise, in patients with rate related conduction abnormalities, such as right bundle branch block (RBBB) or left bundle branch block (LBBB), relative timing of RV and LV peak strain/velocity may widen with exercise.

Timing of regional contractility will thus be affected and likewise the SCFI 220 or VCFI 222 will exhibit a rate dependent variation.

Figure 3:
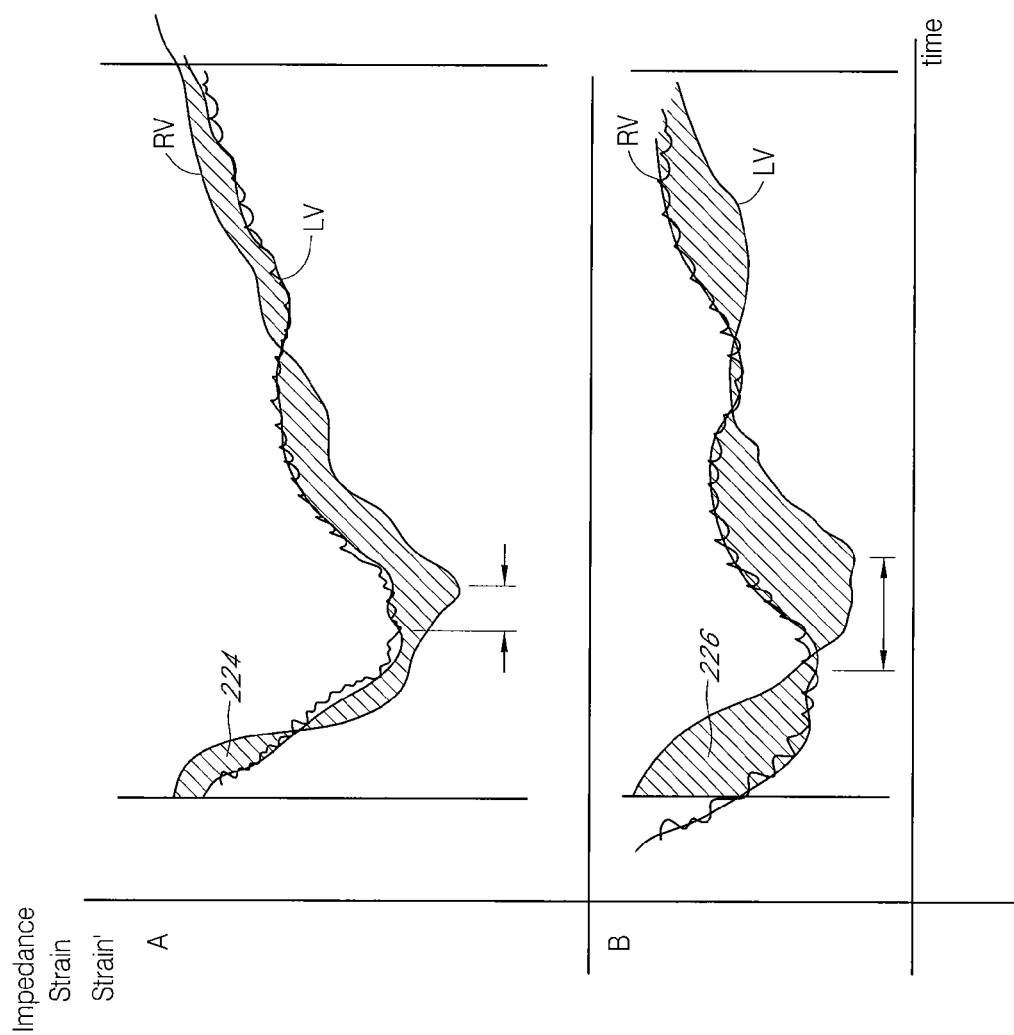
FIG. 3 illustrates schematically two wave forms indicative of a patient's right ventricular and left ventricular activity and illustrating differences in synchronization therebetween.

FIG. 3 illustrates an alternative methodology which can be used to characterize a patient's synchrony characteristics which can be utilized in addition to or as an alternative to the previously described SCFI 220 and/or VCFI 222. In this embodiment, myocardial velocity curves, impedance, and/or strain/strain rate curves are obtained from regions of interest 206, for example in the septum, lateral wall or other myocardial regions to develop curves indicating the activity of the RV and LV. Differences between the RV and LV curves can be integrated over time to obtain an effective area between the curves or difference integrals indicative of the relative synchrony/dysynchrony between the RV and LV.

FIG. 3 illustrates first and second sets of curves A and B and corresponding first and second difference integrals 224, 226 corresponding to the areas of the shaded regions bounded by the RV and LV curves. A visual comparison or quantitative comparison will reveal that the first difference integral 224 is less than the second difference integral 226 indicating a higher degree of synchrony for curves A than for curves B. It will be understood that in other embodiments impedance curves can be obtained to indicate corresponding physiologic activity and impedance curves can likewise be used to develop corresponding difference integrals in other embodiments.

In certain embodiments, one or more measures of a degree of synchrony exhibited by the patient, for example including one or more of the SCFI 220, VCFI 222, and difference integral 224, 226 can be evaluated over a range of patient heart rates to evaluate the synchrony measures as a function of heart rate. For example, SCFI 220 data can be obtained at rest and throughout a range of exercise and/or Dobutamine medication to determine a rate dependent range of values of this measure. It will be expected that in certain implementations SCFI 220 for example will not be a constant value. For example, it would be expected for SCFI 220 to change in a generally asymptotic fashion as RV-LV intervals narrow with exercise. In patients having rate related conduction abnormalities, such as right or left bundle branch blocks, relative timing of RV and LV peak strain/strain velocity changes with exercise and thus affects timing of regional contractility.

In order to improve therapy for dysfunctional patients, including heart failure (HF) patients and those having contractile and/or stimulation deficits, it is important that LV and RV peak contractility be optimally synchronized for the individual patient. It is further important that RV and LV contractility be synchronized or timed appropriately relative to valvular events for optimal hemodynamic performance. Timing of valvular events can be performed by equating the timing of aortic valve opening and closure in parasternal views relative to ECG and/or IEGM data. These timing measurements can be extrapolated to an apical four-chamber view where strain-rate imaging is performed. This enables accurate determination of the isovolumic contraction, the isovolumic relaxation and systolic ejection phase. It is important however that LV-RV synchrony as well as synchrony between ventricular contractility and valvular timing be maintained over a range of heart rate.

Use of measures of patient's contractile synchrony, such as use of CFI 220, VCFI 222 and/or difference integrals 224, 226 provides valuable diagnostic tools and confirming information of the relative degree of individual optimization of programmed timing intervals. For example, collection of data from an eucontractile population can be used to develop normalized or characteristic curves of a healthy population. This can be utilized for comparison purposes with SCFI 220 values determined for a dysfunctional patient.

In dysfunctional patients whose conductivity becomes more impaired, for example, in a rate dependent acute manifestation and/or a long term chronic manifestation due to progressive cardiomyopathy, changes in the patients SCFI 220 would be expected. In case of such manifestations, the amount of pre-excitation in any given specific vector may indicate a need for adjustment over time. In order to detect such changes, the previously described contractile measures, including SCFI 220, VCFI 222, and difference integral 224, 226, can provide the information. However, at least certain of these measures generally indicate presence of the affected patient in a clinical setting to perform measurements, for example echocardiograph or ultrasonic measurements to obtain the contractile measures. It would be advantageous to provide and implement the ability to autonomously and automatically assess a patient's contractile synchrony with reduced need for their presence at a clinical setting, for example, in order to perform ultrasound imaging. It would be particularly advantageous to provide and implement a system that could perform such an autonomous automated process at least partially via an implanted device to further reduce inconvenience for the patient.

Figures 4A, 4B:
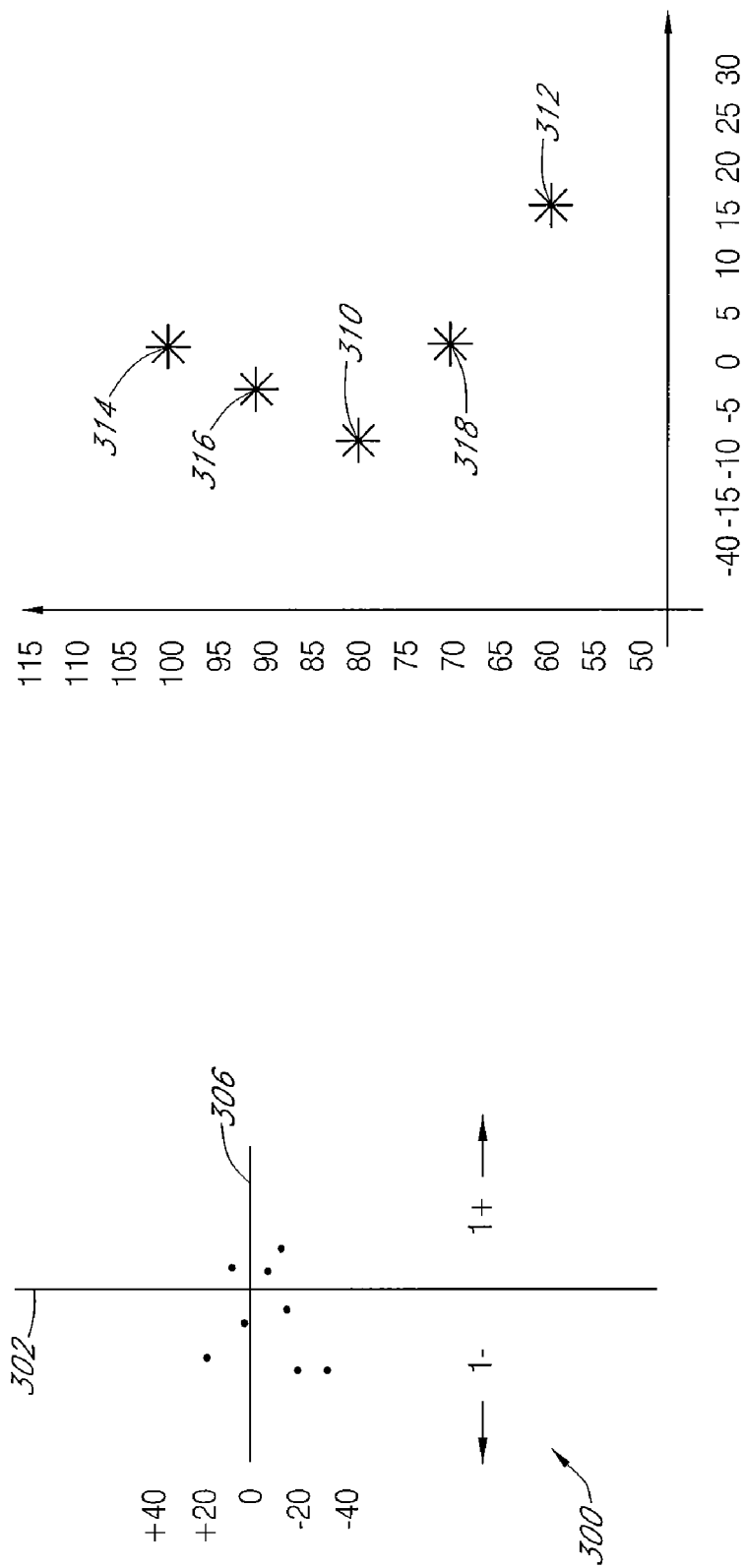
FIG. 4 illustrates schematically optimization or individual adaptation of a plurality of physiologic parameter to select a combination providing improved performance.

FIGS. 4A and 4B illustrates one implementation of a matrix based optimization method 300 adapted to more affectively refine adjustment of therapy delivery by an implantable device for an individual patient's needs and condition. In one embodiment, the method 300 evaluates a patient's physiologic performance, for example, their hemodynamic performance under a variety of combinations of different parameters. The variety of combinations of different values of the parameters can be at least partially conceptualized as a multi-dimensional matrix wherein the method 300 evaluates the patient's physiologic performance at different cells of the matrix.

FIG. 4A illustrates one portion of the method 300 wherein a first variable parameter 302 is evaluated with other variable parameters held constant. In one embodiment, the first parameter 302 comprises a timing parameter such as $V_rV_l$ values. In other embodiments, the first parameter 302 comprises other timing parameters. In yet other embodiments, the first parameter 302 comprises other parameters, such as measured impedance, voltage and/or current of a therapeutic stimulation, a measured potential, etc. In this embodiment, the method 300 evaluates various values of the first parameter 302 and determines a correction factor index 306, for example, the previously described strain correction factor index SCFI 220 and/or a velocity correction factor index VCFI 222. Various values of the first parameter 302 are preferably evaluated which return correction factor index 306 values which are close to 1. However, are previously noted, it will be expected that in certain implementations the correction factor index 306 will approach one but may rarely if ever equal one.

FIG. 4B illustrates another portion of one embodiment of the method 300 wherein the patient's physiologic performance is evaluated at multi-values of a variable first parameter 302 and variable second parameter 304. In one embodiment, the evaluation of the patient's physiologic performance relates to their cardiac performance and this performance can be quantitatively evaluated by measuring an ejection fraction, such as the ecocardiographic measurement via the imager system 202.

In this embodiment, the method 300 includes evaluation of multiple test points indicating different combinations of values of the variable first parameter 302 and second parameter 304. FIG. 4B illustrates that in this embodiment the method evaluates five test points 310, 312, 314, 316, and 318. The first test point 310 corresponds to an AV interval (AVI) of 80 mm and an RV-LV activation of negative 10 milliseconds, e.g., pre-activation of the LV lead by 10 milliseconds. The second test point 312 corresponds to an AVI of 60 milliseconds with an RV-LV activation of plus 15 milliseconds. The third test point 314 reflects substantially simultaneous RV-LV activation or $V_rV_l$ equal to zero. The fourth test point 316 corresponds to an AVI of 90 milliseconds and LV pre-activation by 5 milliseconds. The fifth test point 318 corresponds to simultaneous RV-LV activation with an AVI of 70 milliseconds.

It will be understood that this is simply illustrative and that in other embodiments different combinations of first and second parameters 302, 304 can be evaluated and further that evaluation can be performed for fewer or more test points than the five test points 310, 312, 314, 316, 318 described above. In this illustrated example, the third test point 314, returns the most favorable physiologic performance, e.g., as measured by ejection fraction, indicating that this combination of the first parameter 302 and second parameter 304 provide more optimal physiologic performance.

A further aspect of one embodiment of the method 300 is an iteration of the previously described portions. For example, the matrix based optimization of various combinations of first parameter 302 and second parameter 304 can indicate a more favorable setting, for example, as indicated by the more favorable physiologic performance evaluated for the third test point 314. This can provide a more optimal value for the second parameter 304 which in the illustrated embodiment, corresponds to an AVI of 100 milliseconds. The second parameter 304 can then be held at the more optimal value and a range of the first parameter 302 can be further evaluated for determination of correction factor indices 306 falling closer to one, for example, as previously illustrated and described with respect to FIG. 4A. In certain implementations this can return a more favorable value of the first parameter 302, e.g., one returning a correction factor index 306 closer to one than was evaluated in a first iteration of the method 300.

In a further embodiment, the method 300 can be iterated additional cycles at higher resolution. For example, a first iteration of the method 300 can proceed with graduations between variable settings of the first and/or second parameters 302, 304 of 10 milliseconds. This can be considered to return an initial rough estimate of a more optimal setting of the first and second parameters 302, 304. A second iteration of the method 300 can follow with graduations between the variable settings of the first and/or second parameters 302, 304 for example at five millisecond increments.

As the initial iteration of the method 300 has returned a first more optimal setting of the first and second parameters 302, 304, the second iteration can be considered to fine tune this first more optimal setting and in this embodiment the matrix of values of the first and second parameters 302 and second parameters 302, 304 can include combinations of values of the smaller graduations adjacent the more optimal test point evaluated in the preceding iteration of the method 300. It will be understood that an appropriate number of iterations of the method 300 as well as corresponding resolution or graduation in the variable settings of the first and/or second parameters 302, 304 can be adapted to the needs and limitations of a particular application by one of ordinary skill.

It will be appreciated that in certain implementations, the evaluation of the test points for evaluation of the patient's physiologic performance can involve an extended measurement interval. For example, when evaluating the patient's cardiac performance, the method 300 can observe the patients cardiac output over multiple cardiac cycles. This data can then be summation averaged and the summation averaged data can be evaluated as the indicator of the patient's cardiac performance. Summation averaging over multiple physiologic cycles offers the advantage of suppressing random noise offering a greater signal to noise ratio to more accurately reflect the effect of changes in one or more of the first and second parameters 302, 304. Summation averaging over multiple physiologic cycles also provides an accommodation period to facilitate occurrence of a relatively steady state.

Certain embodiments of the method 300 provide the advantage of reduced need for definition of timing of IC, SCP, and IVR by evaluating parameters indicative of relative optimization of systolic and diastolic function while changes in interval timing occur. For example, ejection fraction (EF) can be based on acoustic measurements to quantify the ejection fraction parameter indicative of cardiac performance.

In another embodiment, three-dimensional assessments of regional contractility such a global systolic contraction amplitude can also be utilized as an indicator of the patient's cardiac performance. In yet another embodiment, the patient's aortic velocity time integral (VTI) can also be utilized in addition to or as an alternative indicator of the patient's cardiac performance.

Figure 5:
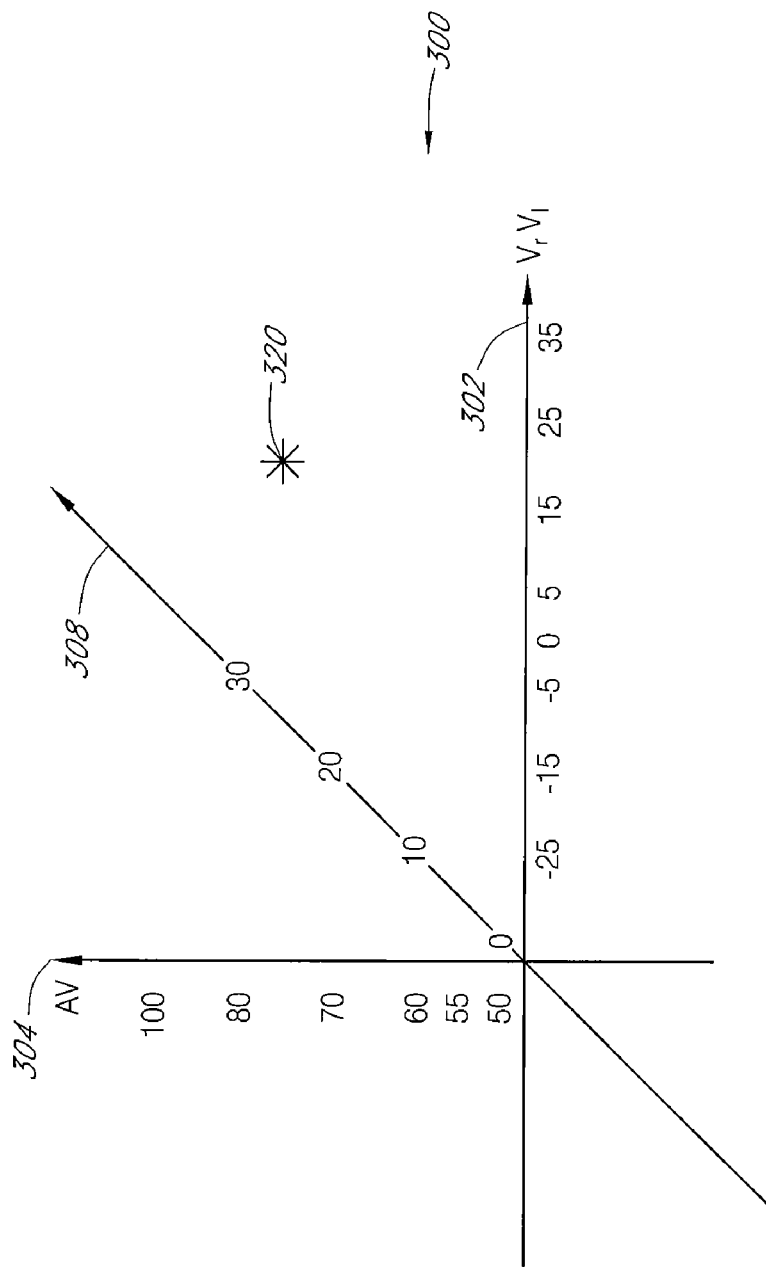
FIG. 5 illustrates one embodiment of a three-dimensional matrix conceptualization of selecting an optimal combination of multiple parameters for improved therapy delivery.

FIG. 5 illustrates a further embodiment of the method 300 employing measures of the patient's cardiac performance such as relative ejection fraction and/or aortic VTI or optimize timing characteristics. In this embodiment, the method 300 can be conceptualized as employing a three-dimensional matrix defined by various combinations of variable values of a first parameter 302, a second parameter 304, and a third parameter 308.

In one embodiment, the first parameter 302 corresponds to a first $V_rV_l$ timing and the second parameter 304 corresponds to an AV interval (AVI). In one embodiment, the third parameter 308 corresponds to timing between right atrial activation and activation in another region, for example a septal region. The third parameter can be defined at least in part by an electrode positioned in or about the right atrium (RA) including but not limited to an RA bipolar electrode pair or electrode pair implementing a high voltage shocking coil, e.g. superior vena cava coil and device can electrode. In another embodiment, the third parameter 308 corresponds to a ventricular-ventricular interval measurement taken along a different vector in embodiments including a multi-site CS lead, indicated as $V_a$-$V_b$.

In a similar manner previously described for a two-dimensional optimization of the first parameter 302 and second parameter 304, this embodiment comprises optimization of three dimensions corresponding to the first, second, and third parameters 302, 304, 308. Also in a similar manner, the patient's physiologic performance is evaluated to determine more optimal combination of the variable first, second, and third parameters 302, 304, 308, such as by evaluation of a measured ejection fraction (EF) or aortic VTI.

Due to the difficulty and limitations of illustrating three dimensional space with a two-dimensional figure, FIG. 5 illustrates a single test point 320 where variable values of the first, second, and third parameters 302, 304, and 308 defining the matrix return a more optimal physiologic performance. It will be understood however that particularly as this embodiment comprises three dimensions or parameters which are evaluated in various combinations, it would generally be the case that multiple test points would be evaluated in determining the more optimal test point 320. In this embodiment, the test point 320 corresponds to a value of the first parameter 302 corresponding to a $V_rV_l$ interval of +20 milliseconds, a second parameter 302 value corresponding to an AVI of 75 milliseconds and a value of the third parameter 308 corresponding to a ventricular-ventricular pacing stimulus interval between two electrode pairs in a multi-site LV pacing lead VaVb of 35 milliseconds.

Figure 6:
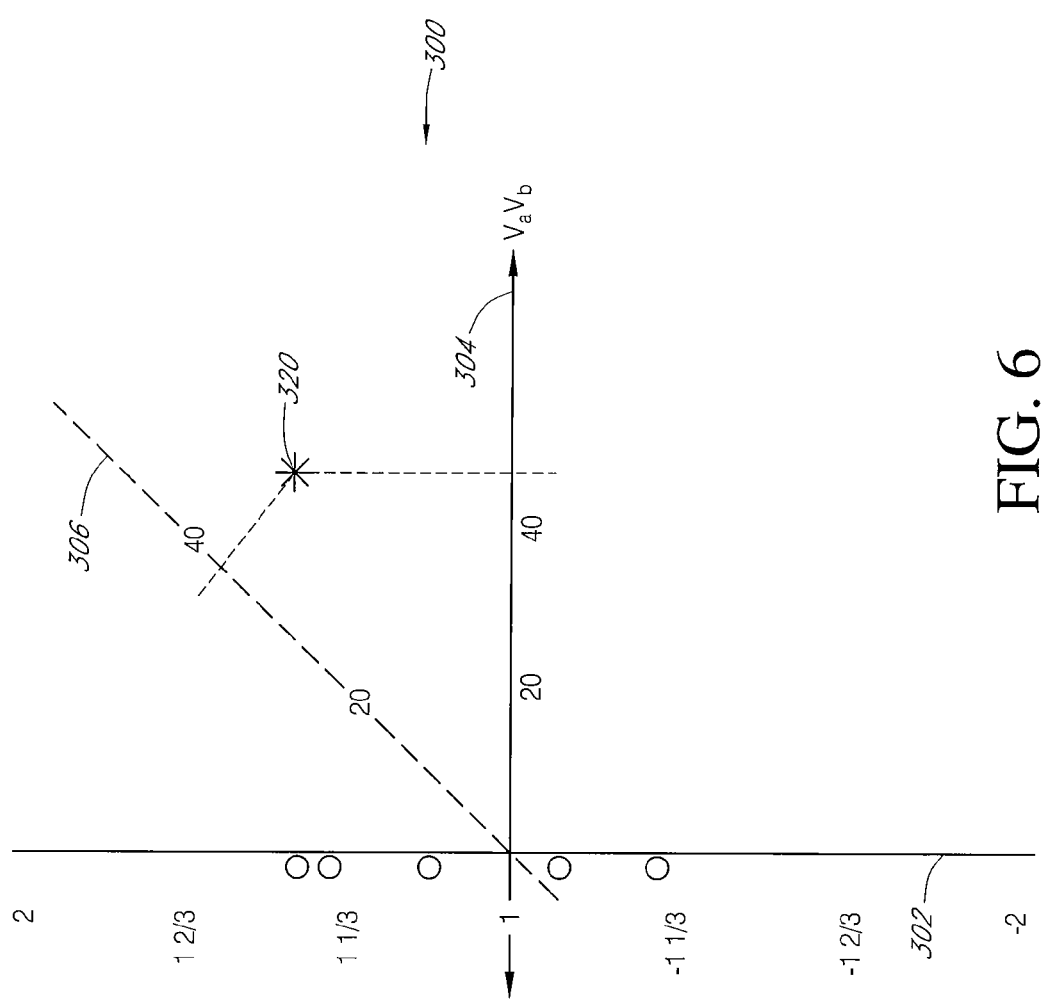
FIG. 6 illustrates schematically one embodiment of a higher order matrix conceptualization of selecting a combination of multiple variable parameters wherein two or more variables are evaluated to create a third dimensionless parameter defining one dimension of the matrix conceptualization.
Figure 7:
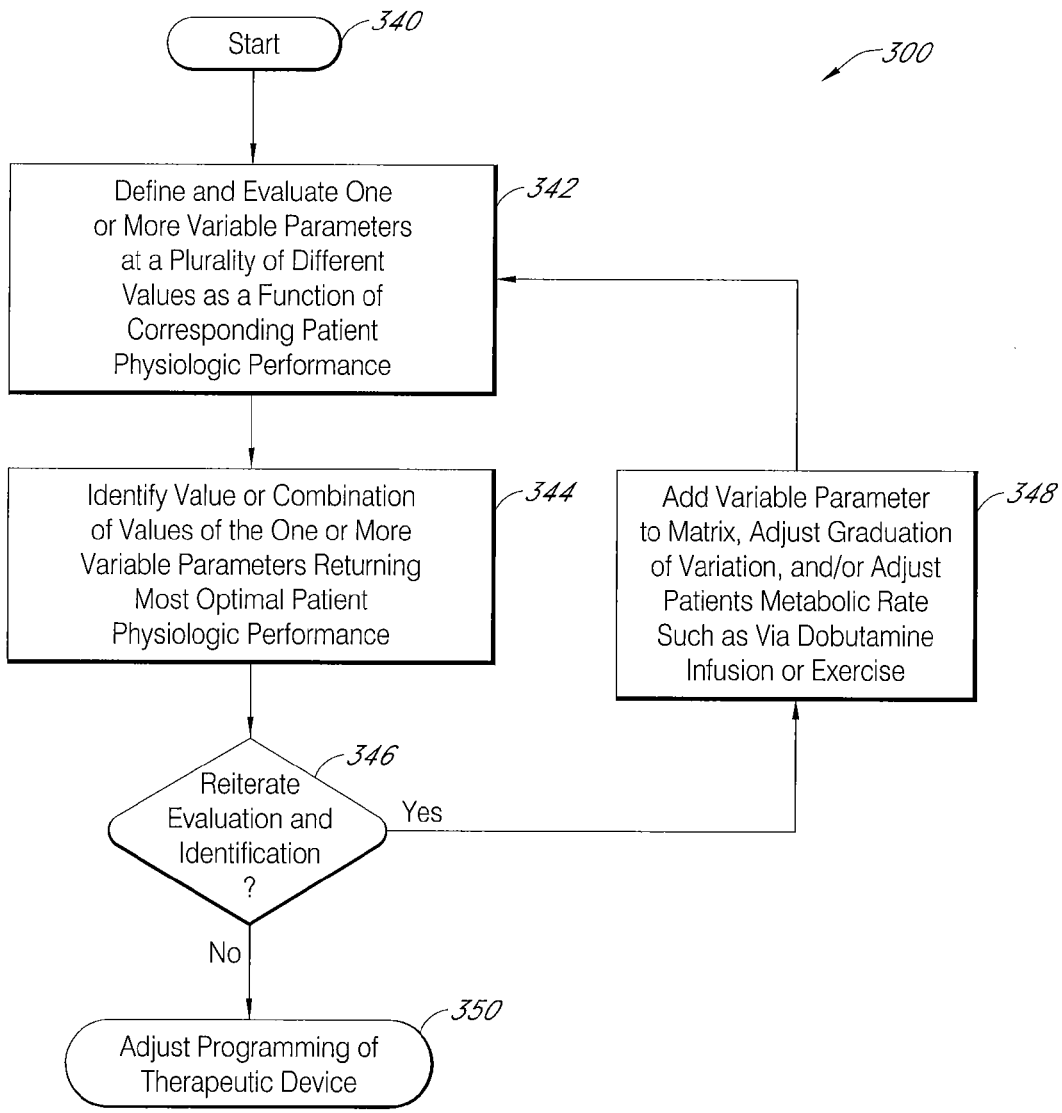
FIG. 7 illustrates a flow chart of one embodiment of methods of individually optimizing multiple variable parameters determining therapy delivery in an implantable medical device for improved performance for the individual patient.

FIG. 6 illustrates yet another embodiment of the method 300 of a higher dimensional conceptualization of a matrix based optimization of multiple variable parameters for improved physiologic performance. In this embodiment, two independent variable parameters, such as $AV_1$ and $V_r\text{-}V_l$, are combined and several combinations of AVI and $V_r\text{-}V_l$ previously found to be favorable for improving cardiac performance are evaluated with an additional parameter. This is indicated as the first parameter 302 defining the vertical or Y-axis of the three dimensional matrix illustrated in FIG. 6. A second parameter 304 corresponding to ventricular-ventricular timing intervals along a different vector indicated generically as $V_aV_b$ defines the X-axis of the three-dimensional matrix illustrated in FIG. 6. The third parameter 308 corresponds in this embodiment to biatrial timing sequences for example as measured between left and right atrial electrode pairs.

Thus, while illustrated as a three-dimensional matrix in FIG. 6, in this embodiment the evaluation of the patient's physiologic performance can be evaluated across various combinations of four variable parameters. Again, due to the difficulties and limitations of illustrating three dimensional space with a two dimensional figure, a single test point 320 corresponding to a combination of the variable parameters returning most optimal physiologic performance is indicated with the remaining multiple test points omitted from view for ease of understanding. Again, the test point 320 corresponds to the combination of the various variable parameters returning a more optimal patient performance and in various embodiments can correspond to a maximal observed aortic VTI or maximal EF.

Aortic VTI is in certain implementations a preferred indicator as measurement of aortic VTI requires only continuous wave Doppler measurements from an apical five chamber view rather than the more time consuming parasternal imaging that would be typically required to ascertain the IC, SEP, and IR intervals demarcated by the timing of valvular events on a different imaging plane. In yet other embodiments, determination of EF from the apical four chamber view would not require use of any other imaging planes. While embodiments of the method 300 involve higher dimensional matrix evaluations of variable parameters which can add complexity to the evaluation, these embodiments provide the significant advantage of reducing the need to define valvular event timing by imaging in additional planes. Thus, these embodiments simplify the tasks of obtaining ultrasonic imaging data and facilitate improvement of overall patient physiologic performance while reducing or even eliminating the need to define valvular event timing, for example, for IC, SEP, and IR determination.

Additional advantages of various embodiments of the method 300 include simplification of adjustment and programming of a therapeutic device. For example, a clinician can develop representative images with the imager system 202 in an apical four chamber view and in certain implementations a five chamber view, for example, to develop aortic VTI. Once sufficient imaging planes have been obtained, the previous described method 300 can proceed in an automatic manner to obtain a more optimal interval timing adjustment for the device based on the previously obtained imager data.

An additional advantage of various embodiments of the method 300 is that it facilitates optimization of one or more variable parameters across a range of patient metabolic rate. For example, the method 300 can be iterated at a rest state to optimize setting of parameters under rest conditions. The method 300 can then be reiterated following Dobutamine infusion or patient exercise to facilitate optimization of setting of the parameters for improved patient physiologic output under elevated metabolic rate conditions. Absent contraindications, it will be generally preferred to perform measurements at an elevated metabolic rate under Dobutamine infusion to reduce the possibility of elevated myopotentials occurring during exercise from confounding measurements and the technical difficulties of obtaining data while the patient is moving and breathing more rapidly during exercise.

As previously noted, it is important that cardiac activity be both self-synchronized and synchronized with valvular events. For example, it is important that the timing of LV and RV peak contractility be synchronized with each other and also occur at an appropriate time relative to valvular events. As previously noted, this can be evaluated in certain implementations by equating the time of aortic valve opening and closing in parasternal views relative to ECG and/or IEGM data and extrapolating these intervals to the apical four chamber view where strain/strain-rate imaging is performed. The isovolumic contraction (IC) and isovolumic relaxation (IR) times as well as the systolic ejection phase (SEP) can thus be accurately determined. While this provides valuable information for diagnosis and for adjustment of programming of an implantable therapy device, use of a relatively large and expensive imaging system, such as an ultrasound imager, along with the indications for a skilled clinical operator of the imager limits use of the method largely to a clinical setting. Additional embodiments however facilitate implementation of individually optimizing variable parameters of an implantable therapy device with reduced reliance on cumbersome and complicated external equipment.

Figure 8:
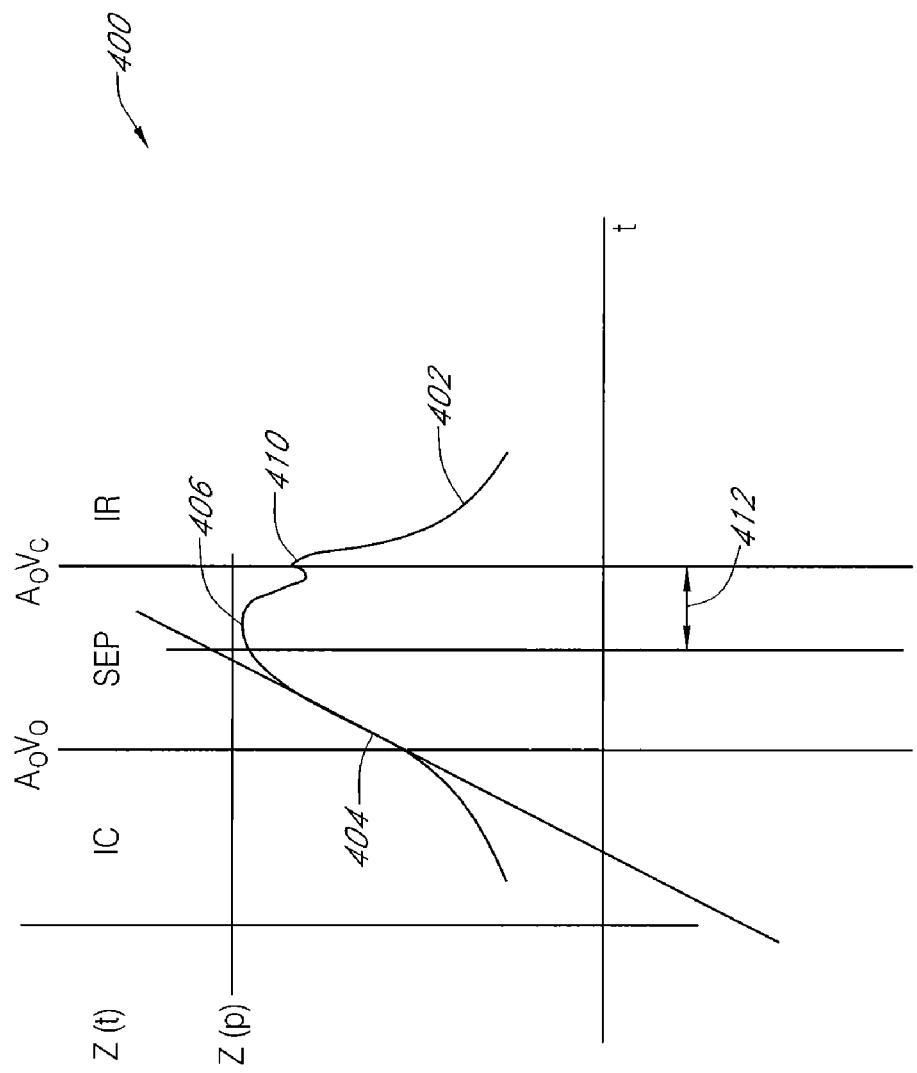
FIG. 8 illustrates one embodiment of an exemplary wave form of a time based impedance measurement portraying systole and diastole and characteristic notching of the impedance wave form corresponding to valvular activity.

FIG. 8 illustrates aspects of a matrix based optimization method of individually adapting or optimizing therapy delivery for an individual patient will be referred to hereafter as method 400 for brevity. The method 400 is at least partially based on analysis of a time varying impedance curve 402 indicative of cardiac impedance and thus cardiac contractility. FIG. 8 illustrates various characteristic aspect or monument of the time-varying impedance 402 indicative of underlying physiologic activity.

In this embodiment, the impedance curve 402 exhibits a peak change dZ/dt 404. The impedance curve 402 also exhibits a peak 406. The impedance curve 402 also exhibits a characteristic notch 410 located approximately at the boundary between the SEP and IR. As the notch 410 corresponds to a region of rapid change in the slope of the impedance curve 402, evaluation for rapid changes in the first derivative dZ/dt and/or second derivative $d^2Z/dt^2$ can be advantageously utilized to identify the location of the notch 410.

It should be noted that analysis of the characteristic features of the impedance curve 402, such as the peak change dZ/dt 404 corresponding to initiation of the SEP and the notch 410 indicate relatively high impedance signal fidelity with relatively low noise and interference. It should further be noted that in certain implementations, for example patients having diseased valves and/or low output states with limited mobility of the valve leaflets, the ability to accurately identify the notch 410 can be limited. It should also be noted that different spatial vector arrangements of sensing electrodes can provide more focused information indicative of specific aspects of cardiac activity.

For example, in one implementation the SVC to RV coil vector can provide more focused signals indicative of tricuspid valve activity. A sensing vector between the coronary sinus and LV electrodes generally traverse the aortic annulus and provide information indicative of aortic valve activity. The sensing vector between the LV lead and SVC coil also provides information indicative of aortic valve opening and closure. The RV tip to LV lateral wall vector generally traverses the mitral valve and can provide information indicative of the activity thereof. A vector between an RV septal lead to a device can or housing generally traverses the RV outflow tract pulmonic valve facilitating gathering of data indicative of the activity thereof. However, further aspects of the method 400 provide the advantage of facilitating individual optimization of variable parameters of a implantable therapy device without requiring direct determination of valvular events, such as an interval 412 between an impedance peak 406 and an aortic notch 410.

Figure 9:
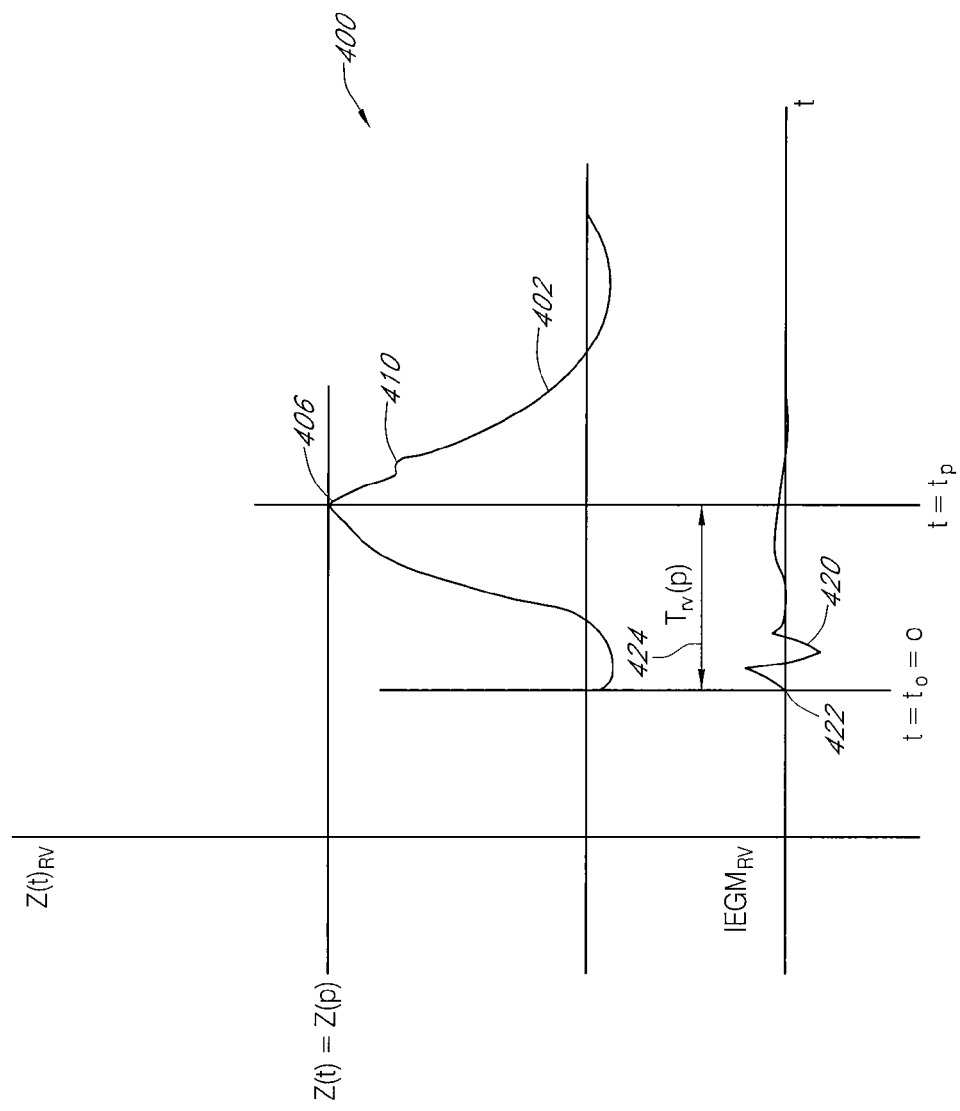
FIG. 9 illustrates a further embodiment of a time varying impedance curve illustrating periods of isovolumic contraction (IC) systolic ejection phase (SEP), and isovolumic relaxation (IR) and an intracardiac electrogram (IEGM) waveform indicating electrochemical activity.

FIG. 9 illustrates additional aspects of embodiments of the method 400 based at least partially on electromechanical coupling intervals for one or more vectors. FIG. 9 illustrates an impedance curve 402 corresponding in this embodiment to the time varying impedance characteristics measured for the right ventricle (RV). FIG. 9 also illustrates a time varying intracardiac electrogram (IEGM) indicative of the electrical characteristics of the patient's cardiac activity. Thus, FIG. 9 illustrates both mechanical (impedance) and electrical characteristics of the patient's cardiac activity. The IEGM curve 420 exhibits an onset 422 also indicated as $T=T_0=0$. A first electromechanical coupling interval 424 is also illustrated in FIG. 9 corresponding to the delay or interval between the onset 422 of the IEGM curve 420 and the peak 406 of the impedance curve 402 corresponding to the patient's RV activity. The first electromechanical coupling interval 424 is also indicated at $T_{RV}(P)$.

Figure 10:
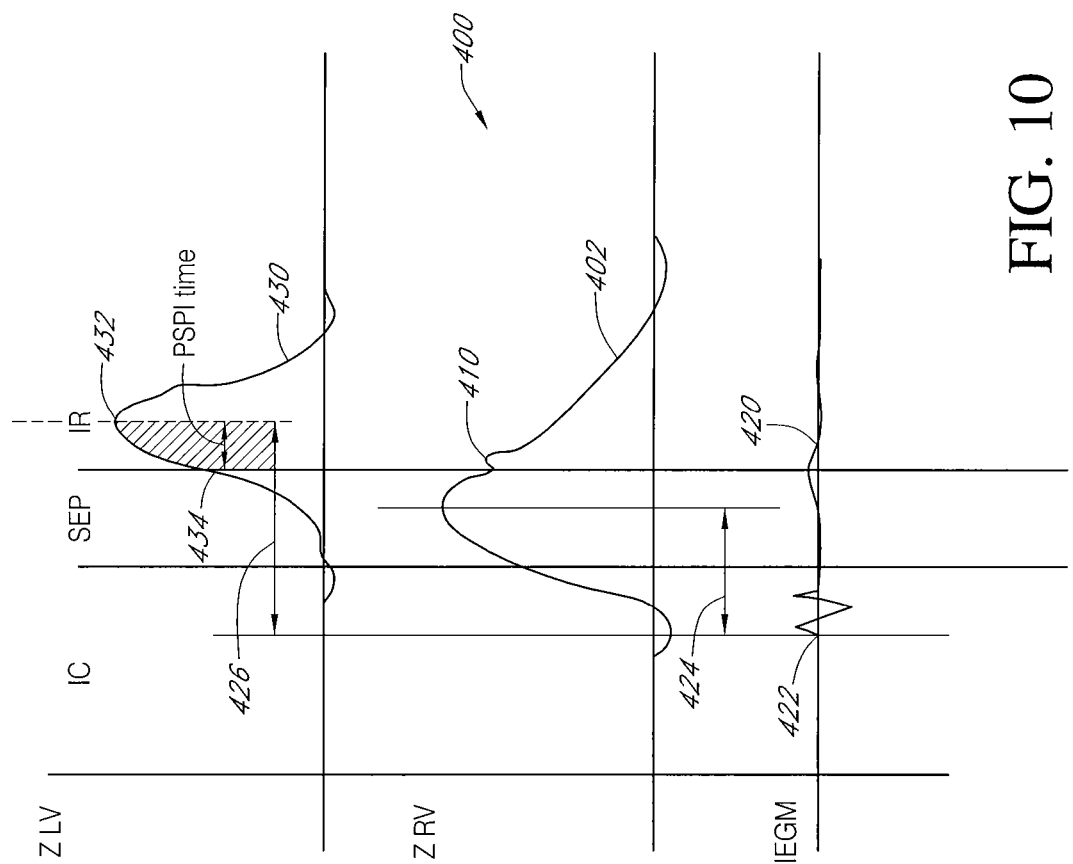
FIG. 10 illustrates exemplary wave forms of a time varying impedance measurements of left and right ventricle activity as well as a corresponding intracardiac electrogram (IEGM).

A similar second electromechanical coupling interval 426 is illustrated in FIG. 10 corresponding to the delay or interval between the onset 422 of the IEGM curve 420 and a peak 432 of an impedance curve 430 corresponding to the patient's left ventricular (LV) activity. FIG. 10 also illustrates a peak change 434 of the patient's LV impedance curve 430 at the transition between the SEP and IR.

In one embodiment, the method 400 defines an electromechanical correction factor index defined equal to the ratio of the first electromechanical coupling interval 424 to the second electromechanical coupling interval 426 or $T_{RV}(P)$ divided by $T_{LV}(P)$. The electromechanical correction factor index (EMCFI) is a dimensionless quantity that will approach a value of 1 for more synchronous contraction between the RV and LV. Thus, the EMCFI is analogous to the SCFI 220 and the VCFI 222 as well as the correction factor index 306 and can be utilized as an indicator of the relative synchrony of the patient's cardiac activity as well as a reliable indicator of their overall cardiac output performance. An advantage of the EMCFI is that the measurements obtained to derive the EMCFI can be obtained via the measurement capabilities of an implantable therapy device without requiring the use of an external device, such as an external imager system 202. This facilitates use of the method 400 on a long term extended basis and iterations of the method 400 need not take place in a clinical setting.

It will be understood that the EMCFI can be obtained at multiple patient metabolic rates, for example, at rest and with exercise—Dobutamine. It will be further understood that EMCFI values can be utilized as additional diagnostic tools and to confirm/evaluate more optimal variable parameter settings for an individual patient.

While the EMCFI value may not equal one in a more optimal combination of settings for an individual patient, it is expected that the EMCFI will approach one for many dysynchronous patients as improvements in their interval timing occur. In addition, while use of the method 400 may not be able to improve underlying intrinsic myocardial contractility, improvements in the functional performance of the patient's heart will be expected. Diastolic filling or lusitropy will improve overall cardiac output by virtue of the Starling mechanism. Similarly, aspects of the method 400 facilitate reduction in pre- or post-systolic myocardial thickening (PSMT). For example, by evaluating the relative magnitudes of the first and second electromechanical coupling intervals 424, 426 $T_{RV}(P)$, $T_{LV}(P)$ can be utilized to determine an appropriate pre-excitation interval for the appropriate stimulation leads. This will result in closer correlation between the first and second electromechanical coupling intervals 424, 426 that will result in an EMCFI value closer to 1 and reduction in PSMT.

Figure 11:
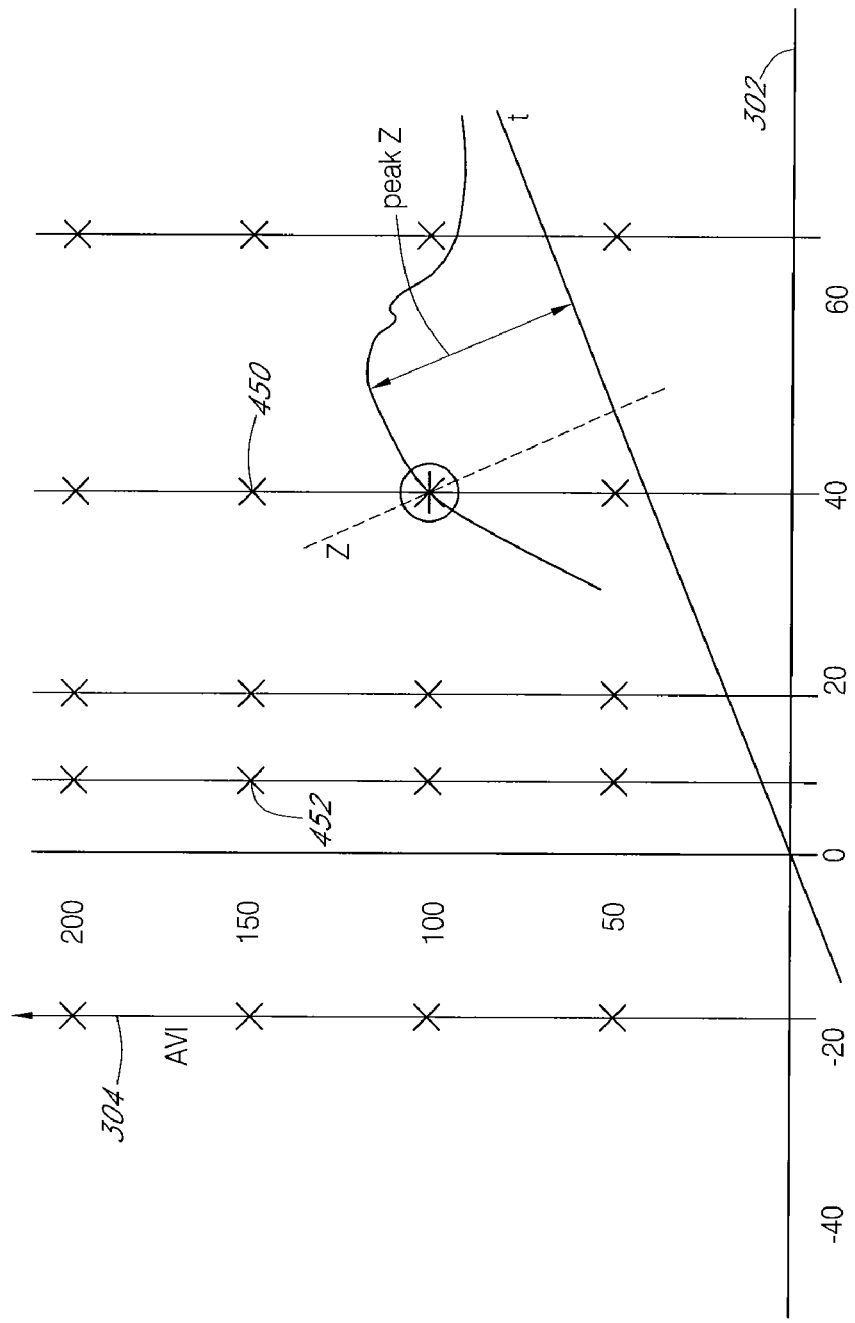
FIG. 11 illustrates another embodiment of a matrix conceptualization of evaluating multiple parameters for improved individual adaptation of therapy delivery.

FIG. 11 illustrates additional aspects of the method 400 including evaluation of multiple combinations of setting of multiple variable parameters effecting therapy delivery by an implantable therapy device and thereby the patient's performance. In this embodiment, an evaluation parameter 450 comprising a value of the second derivative of an impedance measurement, $d^2Z/dt^2$ is utilized as a surrogate or evaluating parameter for the patient's physiologic performance. It will be appreciated that this is simply illustrative of one implementation of the method 400 and that in other embodiments other evaluation parameters 450, such as the EMCFI, indexes of pre- or post-systolic positive impedance indices of lusitropic cardiac performance, systolic cardiac performance, or others can be utilized as evaluation parameters 450 of the patient's physiologic performance. In this embodiment, the method 400 evaluates multiple combinations of variable settings of first and second parameters which will be indicated as the first parameter 302 and second parameter 304 as in certain aspects, the method 400 shares substantial similarity with the method 300.

In this embodiment a first parameter 302 corresponding to $V_R V_L$ intervals are evaluated with a fixed value of the second parameter 304 to determine which variations or settings of the first parameter bring the EMCFI close to 1. In a first aspect, the method 400 further evaluates multiple combinations of various settings of both the first and second parameters 302, 304 at representative test points 452 and the respective evaluation parameter 450 of the test points 452 is evaluated.

In one exemplary embodiment, the evaluation of the method 400 proceeds with graduations of the first parameter corresponding to the $V_R V_L$ of approximately −20, +10, +20, +40, and +70 milliseconds and graduations of the second parameter 304 corresponding to an AVI of approximately 50, 100, 150, and 200 milliseconds. Thus, in this embodiment, 20 test points 452 corresponding to the 20 possible combinations of the graduations of the first and second variable parameters 302, 304 are evaluated for their respective evaluation parameter 450 values. As an illustrative example, in this embodiment a value of the first parameter 302 of +40 milliseconds and a value of the second parameter 304 of 100 milliseconds returns a maximal evaluation parameter 450, in this embodiment a maximal peak $d^2Z/dt^2$ value. This result would then be utilized to adjust the setting of a therapeutic device for improved or optimized performance for the individual patient.

It will be understood that in a similar manner to that previously described for the method 300, in other embodiments of the method 400 additional variable parameters can be evaluated such that the method 400 can be conceptualized as a three, four, or higher dimensional matrix based evaluation of the multiple variable parameters. It will be further understood that as previously described with respect to the method 300, the method 400 can be iterated one or more times, for example, to determine an optimal combination of variable parameter settings for various levels of cardiac metabolic activity. It will be further understood that in certain embodiments, the method 400 can be iterated with delay periods interposed between iterations, for example, to refine the adjustment of therapy following a combination periods where the patient accommodates the revised therapy.

It will be further appreciated that the particular evaluation parameter 450 utilized in any given iteration of the method 400 can vary to provide additional indications of the patient's physiologic performance. As various implementations of the method 400 can proceed based on measurements performed by an implantable therapy device, the method 400 can be considered to describe a true closed loop programming method wherein a device utilizing embodiments of the method 400 is capable of effectively self-monitoring and adjusting its performance in a true closed loop manner.

Figure 12:
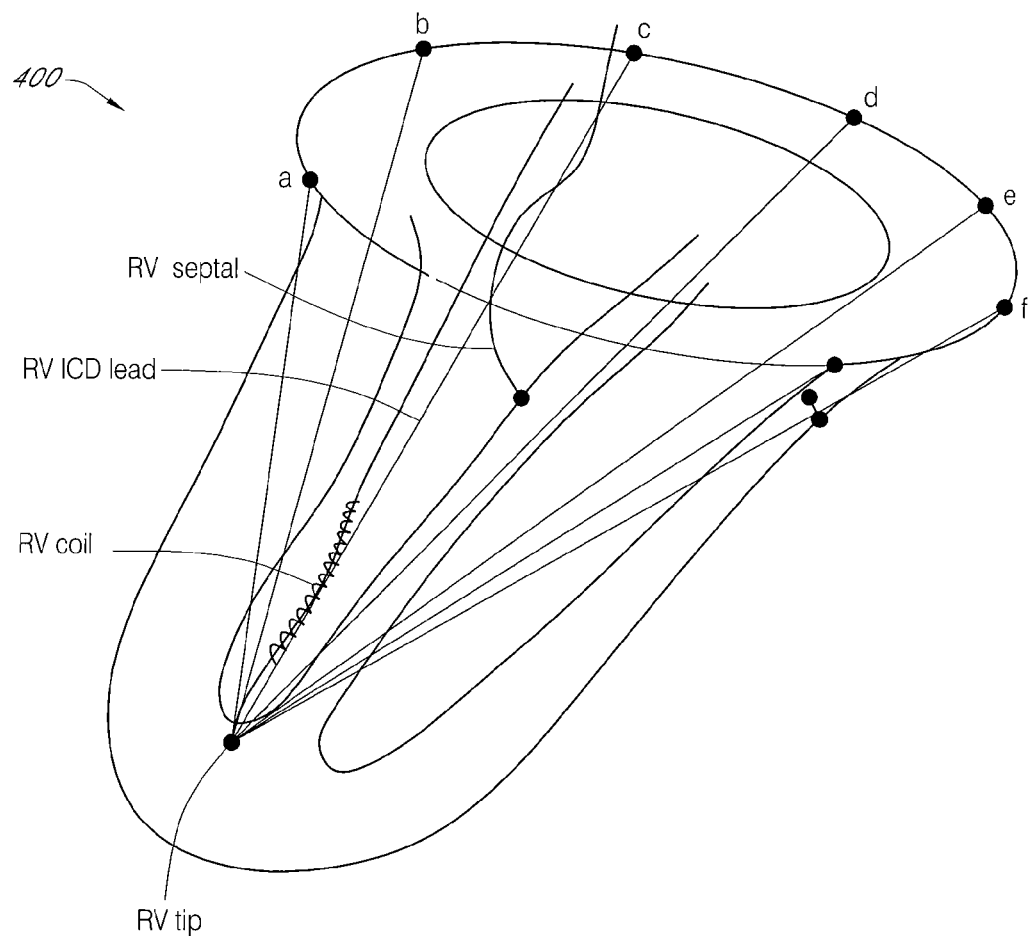
FIG. 12 illustrates one embodiment of multi-site implantable sensors configured to be arranged at multiple sites about a patient's heart to define a plurality of different spatial vectors as well as exemplary wave forms illustrating the spatial temporal characteristics as measured along selected spatial vectors.

FIG. 12 illustrates schematically an arrangement of multiple sensing electrodes arranged about a patient's heart. In this embodiment, an RV lead arranged at a mid-basal septal (anterior) location and an RV ICD lead in combination with a multi-site CS lead define a plurality of sensing locations. A plurality of spatially extending sensing vectors are thereby defined traversing different portions and structural components of the patient's heart. An illustrative indication of these sensing vectors and the time varying impedance signals exhibited therebetween is indicated in the graph between exemplary points of the system indicated simply AB, BC, CD, DC, etc. It will be understood that the actual sensing vectors selected and utilized can be adapted to the needs of a particular patient and the capabilities of a given therapy device. In certain embodiments of the method 400 therefore, the method 400 can be performed or iterated for multiple impedance sensing vectors to provide a more optimal assessment of global myocardial contractility along these multiple vectors. This will facilitate a more optimal synchronization of the patient's cardiac activity and in certain implementations can restore normal helical diastolic and systolic myocardial properties.

Figure 13:
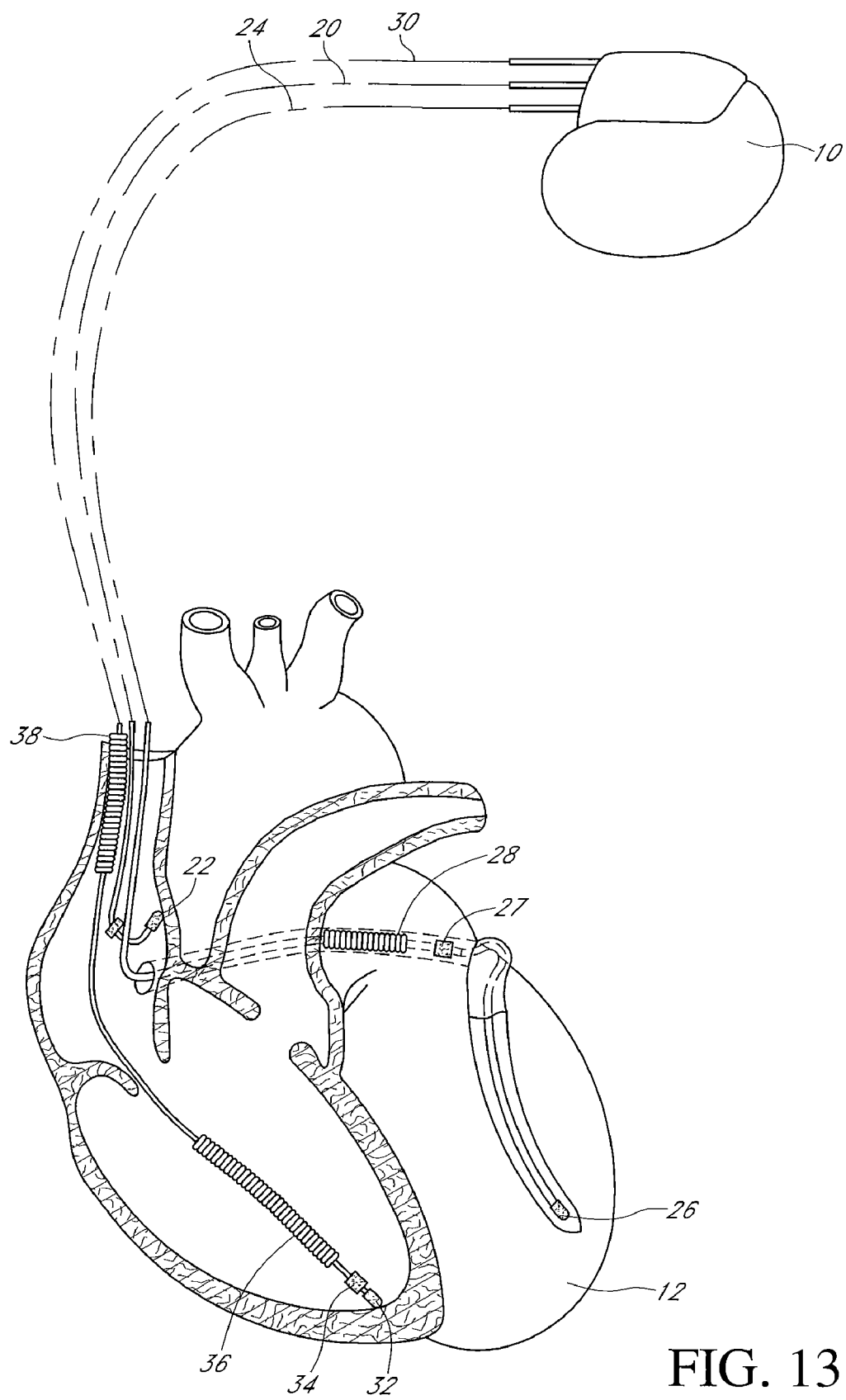
FIG. 13 is a simplified diagram illustrating an implantable stimulation device in electrical communication with at least three leads implanted into a patient's heart for delivering multi-chamber stimulation and shock therapy.

FIG. 13 illustrates one embodiment of an implantable device 10 that can be advantageously employed according to embodiments of the invention previously described. In one embodiment, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 14:
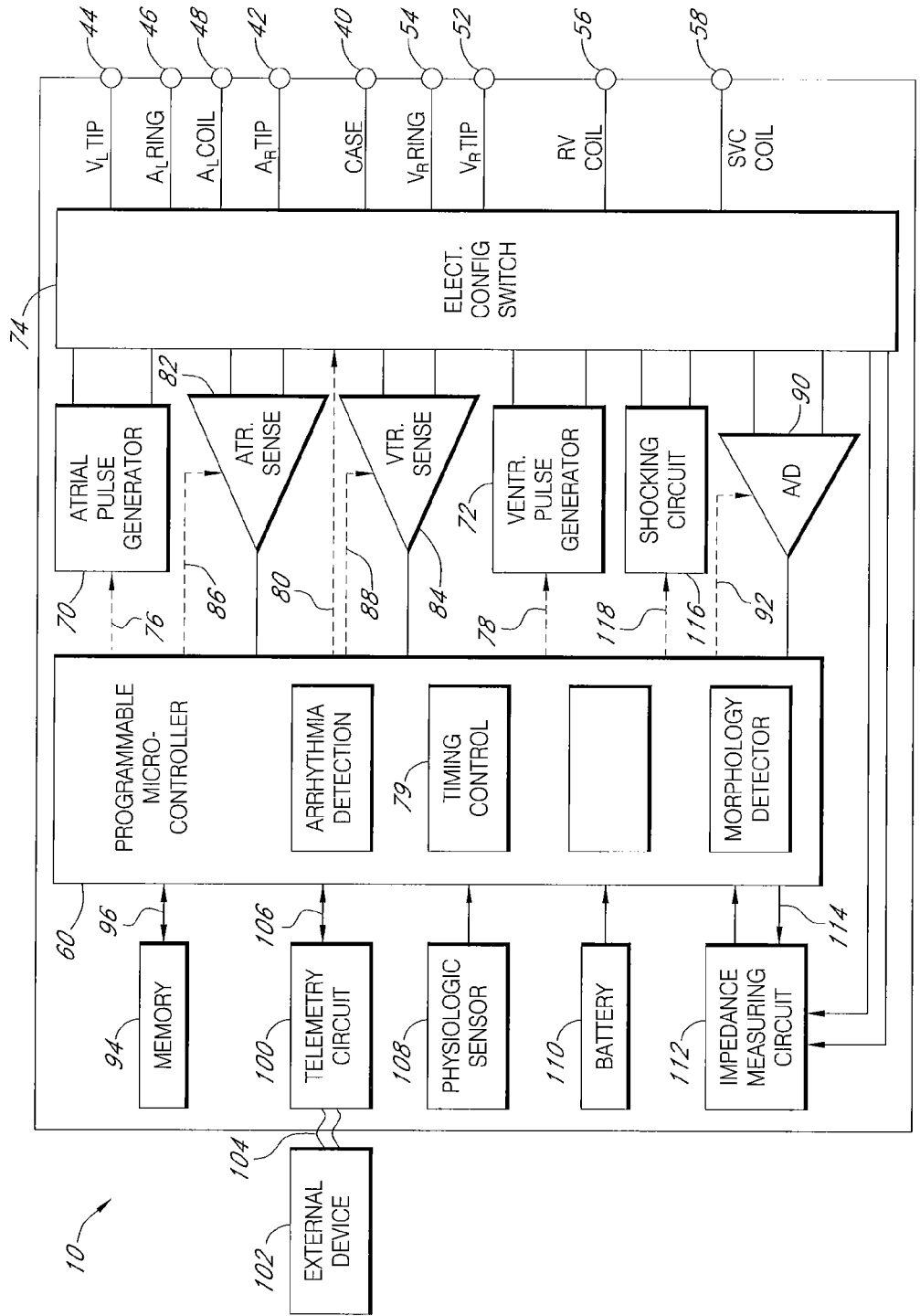
FIG. 14 is a functional block diagram of a multi-chamber implantable stimulation device illustrating the basic elements of a stimulation device which can provide cardioversion, defibrillation and pacing stimulation in four chambers of the heart.

As illustrated in FIG. 14, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 14, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 14, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 14. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 14, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. A method of adjusting therapy delivery in an implantable cardiac stimulation device, the method comprising:

establishing a plurality of setting combinations for at least two variable parameters of the performance of the implantable cardiac stimulation device affecting delivery of therapy;

evaluating at least one aspect of a patient's physiologic performance according to one or more measures under individual ones of the plurality of setting combinations wherein the plurality of setting combinations are selected such that at least one of the two variable parameters vary among the plurality of combinations;

evaluating how changing one of the performance parameters affects how a second performance parameter affects the patient's physiologic performance according to the one or more measures;

selecting a setting combination providing more optimal patient physiologic performance; and iterating the method with the plurality of setting combinations for the at least two variable parameters at a first graduation between settings of the variable parameters to determine a first more optimal setting combination; and reiterating the method with the plurality of setting combinations at a second graduation between settings of the variable parameters to determine a second more optimal setting combination.

2. The method of claim 1, wherein establishing a setting combination comprises setting a timing interval as one or more of the at least two variables affecting therapy delivery.

3. The method of claim 2, wherein setting the timing interval comprises setting an atrioventricular interval (AVI).

4. The method of claim 1, wherein evaluating the patient's physiologic performance comprises imaging the patient with an external imaging system.

5. The method of claim 4, wherein the evaluating further comprises determining an ejection fraction (EF) based on imaging data from the external imaging system.

6. The method of claim 1, wherein evaluating the patient's physiologic performance comprises evaluating internally sensed signals indicative of the patient's cardiac performance.

7. The method of claim 6, wherein evaluating the internally sensed signals comprises evaluating intracardiac electrogram (IEGM) signals indicative of ventricular-ventricular synchrony.

8. The method of claim 1, wherein the evaluating comprises determining a correction factor index representative of ratio of time of peak activation of two dysynchronous regions of a heart and wherein the more optimal setting combination corresponds to a respective correction factor index closest approaching a value of one.

9. A method of adjusting therapy delivery in an implantable cardiac stimulation device, the method comprising:

establishing a plurality of setting combinations for at least two variable parameters of the performance of the implantable cardiac stimulation device affecting delivery of therapy;

evaluating at least one aspect of a patient's physiologic performance according to one or more measures under individual ones of the plurality of setting combinations wherein the plurality of setting combinations are selected such that at least one of the two variable parameters vary among the plurality of combinations;

evaluating how changing one of the performance parameters affects how a second performance parameter affects the patient's physiologic performance according to the one or more measures;

selecting a setting combination providing more optimal patient physiologic performance;

iterating the method at a first patient metabolic rate to determine a first more optimal setting combination;

inducing at least a second metabolic rate of the patient;

reiterating the method at least the second metabolic rate; and determining at least a second more optimal setting combination at the second metabolic rate.

* * * * *